United States Patent
Voigt et al.

(10) Patent No.: US 11,208,664 B2
(45) Date of Patent: Dec. 28, 2021

(54) TRANSCRIPTIONAL SENSOR FOR BILE ACIDS IN BACTEROIDES THETAIOTAOMICRON

(71) Applicant: Massachusetts Institute of Technology, Cambridge, MA (US)

(72) Inventors: Christopher Voigt, Belmont, MA (US); Mao Taketani, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/701,498

(22) Filed: Sep. 12, 2017

(65) Prior Publication Data
US 2018/0073031 A1    Mar. 15, 2018

Related U.S. Application Data

(60) Provisional application No. 62/393,371, filed on Sep. 12, 2016.

(51) Int. Cl.
| | |
|---|---|
| *C12N 15/74* | (2006.01) |
| *A01N 63/00* | (2020.01) |
| *C12Q 1/00* | (2006.01) |
| *C12Q 1/6897* | (2018.01) |
| *C12N 15/63* | (2006.01) |
| *A61K 49/00* | (2006.01) |
| *C07K 14/28* | (2006.01) |
| *C07K 14/00* | (2006.01) |
| *A61K 38/00* | (2006.01) |

(52) U.S. Cl.
CPC .......... *C12N 15/74* (2013.01); *A61K 49/0097* (2013.01); *C07K 14/28* (2013.01); *C12N 15/635* (2013.01); *C12Q 1/6897* (2013.01); *A61K 38/00* (2013.01)

(58) Field of Classification Search
CPC .... C12N 15/74; C12N 15/635; C12Q 1/6897; A61K 49/0097
See application file for complete search history.

(56) References Cited

U.S. PATENT DOCUMENTS

| | | | |
|---|---|---|---|
| 5,874,088 A * | 2/1999 | Mekalanos | |
| 6,242,244 B1 * | 6/2001 | Donohue et al. | |
| 8,137,904 B2 * | 3/2012 | Szalay et al. | |
| 8,212,006 B2 | 7/2012 | Downes et al. | |
| 2015/0166975 A1 | 6/2015 | Prakash et al. | |

FOREIGN PATENT DOCUMENTS

| | | |
|---|---|---|
| EP | 1165135 A1 | 1/2002 |
| WO | WO 2004/076657 A2 | 10/2004 |

OTHER PUBLICATIONS

Rossger et al. Bile acid-controlled transgene expression in mammalian cells and mice. Metabolic Engineering 21:81-90, (Year: 2014).*

Muller et al. Repression of lac promoter as a function of distance, phase and quality of an auxiliary lac operator. J. Mol. Biol. 257:21-29, (Year: 1996).*

Alam et al. Lung surfactant protein B promoter function is dependent on the helical phasing, orientation and combinatorial actions of cis-DNA elements. Gene 282:103-111, (Year: 2002).*

Mimee et al. Programming a human commensal bacterium, Bacteroides thetaiotaomicron, to sense and respond to stimuli in the murine gut microbiota. Cell Systems 1:62-71, (Year: 2015).*

Ruby et al. Complete genome sequence of Vibrio fischeri: A symbiotic bacterium with pathogenic congeners. PNAS 102:3004-3009, (Year: 2005).*

Vingadassalom et al. An unusual primary sigma factor in the Bacteroidetes phylum. Molecular Microbiology 56:888-902, (Year: 2005).*

Xu et al. A genomic view of the human-Bacteroides thetaiotaomicron symbiosis. Science 299:2074-2076, (Year: 2003).*

Horn et al. A novel tightly regulated gene expression system for the human intestinal symbiont Bacteroides thetaiotaomicron. Frontiers in Microbiology, vol. 7, pp. 1-9, (Year: 2016).*

Mastropaolo et al. Comparison of Bacteroides thetaiotaomicron and *Escherichia coli* 16S rRNA gene expression signals. Microbiology 155:2683-2693, (Year: 2009).*

Cerda-Maira et al., Characterization of BreR interaction with the bile response promoters breAB and breR in Vibrio cholerae. J Bacteriol. Jan. 2013;195(2):307-17. doi: 10.1128/JB.02008-12. Epub Nov. 9, 2012.

Cerda-Maira et al., The bile response repressor BreR regulates expression of the Vibrio cholerae breAB efflux system operon. J Bacteriol. Nov. 2008;190(22):7441-52. doi: 10.1128/JB.00584-08. Epub Sep. 5, 2008.

Makishima et al., Vitamin D receptor as an intestinal bile acid sensor. Science. May 17, 2002;296(5571):1313-6.

Park et al., Microbial biosensors: engineered microorganisms as the sensing machinery. Sensors (Basel). May 6, 2013;13(5):5777-95. doi:10.3390/s130505777.

Van Der Velden et al., Monitoring bile acid transport in single living cells using a genetically encoded Förster resonance energy transfer sensor. Hepatology. Feb. 2013;57(2):740-52. doi: 10.1002/hep.26012. Epub Jan. 8, 2013.

Gredell et al., Protein and RNA engineering to customize microbial molecular reporting. Biotechnol J. Apr. 2012;7(4):477-99. doi: 10.1002/biot.201100266. Epub Oct. 26, 2011.

Palmer et al., The repressor protein, Bm3R1, mediates an adaptive response to toxic fatty acids in Bacillus megaterium. J Biol Chem. Jul. 17, 1998;273(29):18109-16.

Stanton et al., Genomic mining of prokaryotic repressors for orthogonal logic gates. Nat Chem Biol. Feb. 2014;10(2):99-105. doi: 10.1038/nchembio.1411. Epub Dec. 8, 2013.

Van Craenenbroeck et al., Episomal vectors for gene expression in mammalian cells. Eur J Biochem. Sep. 2000;267(18):5665-78.

Van De Wiel et al., Real Time Monitoring of Intracellular Bile Acid Dynamics Using a Genetically Encoded FRET-based Bile Acid Sensor. J Vis Exp. Jan. 4, 2016;(107). doi: 10.3791/53659.

Morgan, Plasmids 101: The Promoter Region—Let's Go! Addgene blog. Apr. 3, 2014. Retrieved from https://blog.addgene.org/plasmids-101-the-promoter-region on May 20, 2019.

PCT/US2017/051061, Nov. 29, 2017, International Search Report and Written Opinion.

\* cited by examiner

*Primary Examiner* — Quang Nguyen

(74) *Attorney, Agent, or Firm* — Wolf, Greenfield & Sacks, P.C.

(57) ABSTRACT

The present disclosure relates, in some aspects, to bile acid sensors.

17 Claims, 8 Drawing Sheets

Specification includes a Sequence Listing.

SEQUENCE LISTING

<160> NUMBER OF SEQ ID NOS: 19

<210> SEQ ID NO 1
<211> LENGTH: 630
<212> TYPE: DNA
<213> ORGANISM: Artificial Sequence
<220> FEATURE:
<223> OTHER INFORMATION: BreR-Bt codon optimized for use in B.
      thetaiotamicron

<400> SEQUENCE: 1

| | | | | | |
|---|---|---|---|---|---|
| atgaaattgt | ctgaacagaa | acgtttggct | ttgatcgaag | ctgctaaaga | agaattcact | 60 |
| cagttcggtt | tccacgctgc | taacatggac | cgtgtatgtg | aacgtgctgg | tacttctaaa | 120 |
| cgtactttgt | accgtcactt | cacttctaaa | gaattgttgt | tcatcgaagt | aatcaacttg | 180 |
| ttggtagctc | agccgcacaa | agtaggtttc | gaataccagt | ctactcgttc | tttggctgac | 240 |
| cagttgcacg | actacttcgc | tgctaaaatc | gacttgttgt | accgtactat | cggtttggac | 300 |
| gtattgcgta | tgatcgtagg | tgaattcgta | cgtgacccgg | ctttgactca | gcagtacttg | 360 |
| gctttgatgg | gtactcagga | cactgctttg | actgcttggt | tgcaggctgc | tatcaaagac | 420 |
| ggtaaattga | tcgaaaaaga | agtagctccg | atggctacta | cttttgatgaa | cttgttccac | 480 |
| ggtcagttct | gtggccgca | gttgttggct | gctgtagaat | gccggacgc | taaacagcag | 540 |
| cagatcatga | tggacgaaat | catccgtgta | ttcgtattgt | cttacggtgt | atcttctccg | 600 |
| tctcacttgt | ctatcgaatt | gaaaccgtaa | | | | 630 |

<210> SEQ ID NO 2
<211> LENGTH: 612
<212> TYPE: DNA
<213> ORGANISM: Artificial Sequence
<220> FEATURE:
<223> OTHER INFORMATION: VFA0359-Bt codon optimized for use in B.
      thetaiotamicron

<400> SEQUENCE: 2

| | | | | | |
|---|---|---|---|---|---|
| atgcagaaaa | aattgactcg | ttctcagcag | aaacacttgg | acatcatcaa | cgctgctaaa | 60 |
| gaagaattca | tcgaattcgg | tttcttggct | gctaacatgg | accgtatcac | ttcttctgct | 120 |
| gaagtatcta | aacgtacttt | gtaccgtcac | ttcgaatcta | agaagtatt | gttcgaatct | 180 |
| gtattgacta | tcatcaacga | ctctgtaaac | gaatctatct | cttaccactt | cgacccgaac | 240 |
| aaatctactg | aagaacagtt | gactgaaatc | gcttacaaag | aaatcgacgt | attgtacaaa | 300 |
| acttacggta | tcgctttggc | tcgtactatc | gtaatggaat | tcttgcgtca | gccggaaatg | 360 |
| gctaaaactt | tgatccagaa | catctactct | atccgtgcta | tcactcagtg | gttccgttct | 420 |
| gctatcgaag | ctaaacgttt | gaaagacgct | gacccgaaat | tgatgactga | cgtatacgta | 480 |
| tctttgttcc | agggtttgtt | cttctggccg | caggtaatgc | acttggactt | ggaaccgcac | 540 |
| ggtgaagaat | gtctcagaa | aatcgaaact | ttgactacta | tcttcttgca | gtcttacggt | 600 |
| gtagctgaat | aa | | | | | 612 |

<210> SEQ ID NO 3
<211> LENGTH: 283
<212> TYPE: DNA
<213> ORGANISM: Artificial Sequence
<220> FEATURE:
<223> OTHER INFORMATION: BT1311 Constitutive promoter+RBS

<400> SEQUENCE: 3

| | | | | | |
|---|---|---|---|---|---|
| tgatctggaa | gaagcaatga | aagctgctgt | taagtctccg | aatcaggtat | tgttcctgac | 60 |
| aggtgtattc | ccatccggta | aacgcggata | ctttgcagtt | gatctgactc | aggaataaat | 120 |
| tataaattaa | ggtaagaaga | ttgtaggata | agctaatgaa | atagaaaaag | gatgccgtca | 180 | cacaacttgt cggcattctt ttttgtttta ttagttgaaa atatagtgaa aaagttgcct    240 aaatatgtat gttaacaaat tatttgtcgt aactttgcac tcc    283

<210> SEQ ID NO 4
<211> LENGTH: 32
<212> TYPE: DNA
<213> ORGANISM: Artificial Sequence
<220> FEATURE:
<223> OTHER INFORMATION: Bacteroides consensus promoter sequence
<220> FEATURE:
<221> NAME/KEY: misc_feature
<222> LOCATION: (5)..(24)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t

<400> SEQUENCE: 4
tttgnnnnnn nnnnnnnnnn nnnntanntt tg    32

<210> SEQ ID NO 5
<211> LENGTH: 24
<212> TYPE: DNA
<213> ORGANISM: Artificial Sequence
<220> FEATURE:
<223> OTHER INFORMATION: BreR consensus sequence
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 5
aangtanacn nnnnngtnta cntt    24

<210> SEQ ID NO 6
<211> LENGTH: 116
<212> TYPE: DNA
<213> ORGANISM: Artificial Sequence
<220> FEATURE:
<223> OTHER INFORMATION: PbreR (Bile acid inducible promoter)

<400> SEQUENCE: 6
ttacaaagaa aattcgacaa actgttattt ttctatctat ttaaatgtac acccgtttgt    60
ttactttact ttagttatgt acctttgtcg gcaatgtaca cccgaaagtt tacttt    116

<210> SEQ ID NO 7
<211> LENGTH: 122
<212> TYPE: DNA
<213> ORGANISM: Artificial Sequence
<220> FEATURE:
<223> OTHER INFORMATION: PcfxA (Constitutive promoter+RBS)

```
<400> SEQUENCE: 7
ttacaaagaa aattcgacaa actgttattt ttctatctat ttatttgggt gggaaacttt      60
agttatgtac ctttgtcggc aaataaagat attctcgtca acaaatata aataatataa      120 ac                                                                     122

<210> SEQ ID NO 8
<211> LENGTH: 43
<212> TYPE: DNA
<213> ORGANISM: Artificial Sequence
<220> FEATURE:
<223> OTHER INFORMATION: rpiL* (RBS)

<400> SEQUENCE: 8
cgcattttaa aataaaataa attatttatt taattaaacg aat                       43

<210> SEQ ID NO 9
<211> LENGTH: 516
<212> TYPE: DNA
<213> ORGANISM: Artificial Sequence
<220> FEATURE:
<223> OTHER INFORMATION: NanoLuc Luciferase reporter

<400> SEQUENCE: 9
atggttttta ctctggaaga ttttgttggc gattggcgtc agaccgcggg ttataatttg      60
gatcaagtcc tggaacaggg tggcgtaagc tctctgttcc agaacctggg tgtgagcgtg     120
acgccgattc agcgcatcgt tctgtccggc gagaacggtc tgaaaattga tattcatgtg     180
atcatcccgt acgaaggcct gagcggtgac caaatgggtc aaatcgagaa aatctttaaa     240
gtcgtctacc cagttgacga tcaccacttc aaggttatct tgcattacgg tacgctggtg     300
attgatggtg tgaccccgaa tatgattgac tatttcggcc gtccgtatga aggcattgcc     360 gttttttgacg gtaaaaagat caccgtcacc ggtaccctgt ggaatggcaa taagattatt     420
gacgagcgtc tgattaaccc ggacggcagc ctgctgttcc gcgtgaccat caacggtgtc     480
acgggttggc gtctgtgcga gcgcatcctg gcataa                              516

<210> SEQ ID NO 10
<211> LENGTH: 24
<212> TYPE: DNA
<213> ORGANISM: Artificial Sequence
<220> FEATURE:
<223> OTHER INFORMATION: operator in the -33 element

<400> SEQUENCE: 10
aatgtacacc cgtttgttta cttt                                            24

<210> SEQ ID NO 11
<211> LENGTH: 24
<212> TYPE: DNA
<213> ORGANISM: Artificial Sequence
<220> FEATURE:
<223> OTHER INFORMATION: operator downstream of the -7 element

<400> SEQUENCE: 11
aatgtacacc cgaaagttta cttt                                            24

<210> SEQ ID NO 12
<211> LENGTH: 21
<212> TYPE: DNA
<213> ORGANISM: Artificial Sequence
<220> FEATURE:
<223> OTHER INFORMATION: primer oMT113
```

<400> SEQUENCE: 12
cgctactctc tacgttcaac c                                              21

<210> SEQ ID NO 13
<211> LENGTH: 23
<212> TYPE: DNA
<213> ORGANISM: Artificial Sequence
<220> FEATURE:
<223> OTHER INFORMATION: primer oMT114

<400> SEQUENCE: 13
tgaaatacag tgtaattgtg gcg                                            23

<210> SEQ ID NO 14
<211> LENGTH: 20
<212> TYPE: DNA
<213> ORGANISM: Artificial Sequence
<220> FEATURE:
<223> OTHER INFORMATION: primer oMT115

<400> SEQUENCE: 14
ttcacttcca tcccggttcg                                                20

<210> SEQ ID NO 15
<211> LENGTH: 20
<212> TYPE: DNA
<213> ORGANISM: Artificial Sequence
<220> FEATURE:
<223> OTHER INFORMATION: primer oMT116

<400> SEQUENCE: 15
cacatcgcca gggtccatta                                                20

<210> SEQ ID NO 16
<211> LENGTH: 20
<212> TYPE: DNA
<213> ORGANISM: Artificial Sequence
<220> FEATURE:
<223> OTHER INFORMATION: primer oMT242

<400> SEQUENCE: 16
ccaacaacaa gcacactcca                                                20

<210> SEQ ID NO 17
<211> LENGTH: 20
<212> TYPE: DNA
<213> ORGANISM: Artificial Sequence
<220> FEATURE:
<223> OTHER INFORMATION: primer oMT243

<400> SEQUENCE: 17
tgcgaatggt agaaaagccc                                                20

<210> SEQ ID NO 18
<211> LENGTH: 20
<212> TYPE: DNA
<213> ORGANISM: Artificial Sequence
<220> FEATURE:
<223> OTHER INFORMATION: primer oMT244

<400> SEQUENCE: 18
gacctgcaaa cgaccaaagt                                                20

```
<210> SEQ ID NO 19
<211> LENGTH: 579
<212> TYPE: DNA
<213> ORGANISM: Artificial Sequence
<220> FEATURE:
<223> OTHER INFORMATION: BM3R1 coding sequence

<400> SEQUENCE: 19
atggaaagca cccccgaccaa acagaaagca atttttagcg caagcctgct gctgtttgca      60
gaacgtggtt ttgatgcaac caccatgccg atgattgcag aaaatgcaaa agttggtgca     120
ggcaccattt atcgctattt caaaaacaaa gaaagcctgg tgaacgaact gtttcagcag     180
catgttaatg aatttctgca gtgtattgaa agcggtctgg caaatgaacg tgatggttat     240
cgtgatggct ttcatcacat ttttgaaggt atggtgacct ttaccaaaaa tcatccgcgt     300
gcactgggtt ttatcaaaac ccatagccag ggcacctttc tgaccgaaga aagccgtctg     360
gcatatcaga aactggttga atttgtgtgc acctttttc gtgaaggtca gaaacagggt     420
gtgattcgta atctgccgga aaatgcactg attgcaattc tgtttggcag ctttatggaa     480
gtgtatgaaa tgatcgagaa cgattatctg agcctgaccg atgaactgct gaccggtgtt     540
gaagaaagcc tgtgggcagc actgagccgt cagagctaa                            579
```

TRANSCRIPTIONAL SENSOR FOR BILE ACIDS IN BACTEROIDES THETAIOTAOMICRON

RELATED APPLICATION

This application claims the benefit under 35 U.S.C. § 119(e) of U.S. provisional application No. 62/393,371, filed Sep. 12, 2016, which is incorporated by reference herein in its entirety.

GOVERNMENT SUPPORT

This invention was made with Government support under Grant No. P50 GM098792 awarded by the National Institutes of Health. The Government has certain rights in the invention.

FIELD OF THE DISCLOSURE

The present disclosure relates, in some aspects, to bile acid sensors.

BACKGROUND

Bile acids are steroid acids synthesized from cholesterol in the liver, and stored in the gall bladder in the form of conjugated bile acids, mostly cholic acid and chenodeoxycholic acid (called primary bile acids) conjugated to a glycine or a taurine group. After a meal, the conjugated bile acids are released through the bile duct into the jejunum of the small intestine to aid in digestion of dietary fats. Although ~97% of the bile acids are actively absorbed back into the liver through the hepatic circulation, ~3% of the bile acids enter the colon and there they are thoroughly modified by the resident gut microbiota. The dominant actions of these resident gut bacteria include deconjugation (removal of the glycine or taurine by bile salt hydrolase) and 7α-dehydroxylation (removal of the OH group in the 7α position) of the primary bile acids yielding secondary bile acids deoxycholic acid (DCA; from 7α-dehydroxylation of cholic acid) and lithocholic acid (LCA; from 7α-dehydroxylation of chenodeoxycholic acid). Interestingly, secondary bile acids, the bacterial derived bile acids, are implicated to be causative agents for colon and liver cancer, as well as being a candidate disease marker for inflammatory bowel disease.

Currently, two methods of directly detecting bile acid levels exist. One is an enzymatic assay where $NAD^+$ dependent steroid dehydrogenase enzyme is used to oxidize bile acids. By measuring the levels of NADH formed from the oxidative reaction, levels of bile acids are indirectly quantified. The second method of detection is through chromatography, where extraction, deconjugation and derivatization are performed followed by quantification using gas chromatography-mass spectrometry and liquid chromatography-mass spectrometry.

SUMMARY OF THE DISCLOSURE

Bile acids are steroid acids derived from cholesterol in the liver, are released into the gastrointestinal tract to aid in digestion and are thoroughly modified by the resident gut microbiota. Bile acids act as versatile signaling molecules with a variety of endocrine functions and are linked to metabolic disease and cancer. Disclosed herein is an engineered transcriptional sensor for bile acids in the human gut symbiont *Bacteroides*, a candidate chassis for long-term cell-based diagnostics and therapeutics for the human gastrointestinal tract.

Disclosed herein are engineered nucleic acid molecules that are sensors for bile acids, and engineered cells containing such nucleic acid molecules, including the human gut symbiont *Bacteroides thetaiotaomicron*. The engineered nucleic acid molecules and engineered cells can detect and report the presence and/or concentration of bile acids such as deoxycholic acid (DCA), lithocholic acid (LCA), chenodeoxycholic acid (CDCA), and cholic acid (CA). Sensing these clinically important compounds provides novel cell-based diagnostics and therapeutics.

The present disclosure includes the unexpected finding that the bile acid sensors BreR and VFA0359 are functional in *Bacteroides*.

According to one aspect, engineered nucleic acid molecules are provided. The engineered nucleic acid molecules include: (a) a nucleotide sequence encoding a bile acid sensor protein that binds to a bile acid, (b) a constitutive promoter that is operably linked to the nucleotide sequence encoding the bile acid sensor protein, (c) a bacteria specific promoter, (d) one or more operators that is/are inserted in or near the bacteria specific promoter region and to which the bile acid sensor protein can bind, and (e) a nucleotide sequence encoding an output molecule that is operably linked to the one or more operators and bacteria specific promoter; wherein binding of the bile acid sensor protein to the operator results in inhibition of transcription of the nucleic acid encoding the output protein.

In some embodiments, the bile acid sensor protein is BreR or a homolog thereof. In some embodiments, the BreR is from *Vibrio cholera*. In some embodiments, the nucleic acid encoding the BreR comprises a nucleotide sequence that is at least 95% identical to SEQ ID NO: 1. In some embodiments, the nucleic acid encoding the BreR comprises a nucleotide sequence that is SEQ ID NO: 1. In some embodiments, the homolog of BreR is VFA0359 from *Vibrio fischeri*. In some embodiments, the nucleic acid encoding the VFA0359 comprises a nucleotide sequence that is at least 95% identical to SEQ ID NO: 2. In some embodiments, the nucleic acid encoding the BreR comprises a nucleotide sequence that is SEQ ID NO: 2.

In some embodiments, the bile acid is a deconjugated bile acid. In some embodiments, the deconjugated bile acid is deoxycholic acid or lithocholic acid.

In some embodiments, the constitutive promoter is *B. thetaiotaomicron* promoter BT1311. In some embodiments, the nucleotide sequence of the *B. thetaiotaomicron* promoter BT1311 is at least 95% identical to SEQ ID NO: 3. In some embodiments, the nucleotide sequence of the *B. thetaiotaomicron* promoter BT1311 is SEQ ID NO: 3.

In some embodiments, the bacteria specific promoter is a *Bacteroides* specific promoter. In some embodiments, the nucleotide sequence of the *Bacteroides* specific promoter is at least 95% identical to SEQ ID NO: 4. In some embodiments, the nucleotide sequence of the *Bacteroides* specific promoter is SEQ ID NO: 4.

In some embodiments, the one or more operators are two BreR operators. In some embodiments, the BreR operator comprises a nucleotide sequence that is at least 95% identical to SEQ ID NO: 5. In some embodiments, the BreR operator comprises a nucleotide sequence that is SEQ ID NO: 5, SEQ ID NO: 10 and/or SEQ ID NO: 11.

In some embodiments, the output molecule is a protein. In some embodiments, the protein is a detectable protein, therapeutic protein or a transcription factor that induces the expression of a detectable molecule or therapeutic molecule. In some embodiments, the detectable protein is a fluorescent protein, bioluminescent protein, an enzyme that provides formation of a colored product that can be visualized, or a functional peptide or polypeptide thereof. In some embodiments, the bioluminescent protein is firefly luciferase, click-beetle luciferase, *Renilla* luciferase or luciferase from *Oplophorus gracilirosiris*. In some embodiments, the therapeutic protein is an anti-tumor protein or an anti-inflammatory protein.

In some embodiments, the output molecule is a nucleic acid.

According to another aspect, expression vectors are provides that include the engineered nucleic acid molecules described herein.

According to another aspect, genetically modified bacteria are provided. The genetically modified bacteria include the engineered nucleic acid molecules described herein or the expression vectors described herein.

In some embodiments, the engineered nucleic acid molecule is integrated in the genome of the bacterium.

In some embodiments, the bacterium is a human gut symbiont. In some embodiments, the bacterium is a *Bacteroides* bacterium. In some embodiments, the *Bacteroides* bacterium is *Bacteroides thetaiotaomicron*.

According to another aspect, compositions are provided that include a plurality of the genetically modified bacteria described herein. According to another aspect, pharmaceutical compositions for oral administration are provided including the compositions and a pharmaceutically acceptable carrier.

According to another aspect, methods of monitoring bile acid in the gut of a subject are provided. The methods include administering to the subject the compositions or the pharmaceutical compositions described herein.

According to another aspect, methods of determining the level of bile acid in a biological sample obtained from a subject are provided. The methods include incubating the compositions described herein with the biological sample. In some embodiments, the bile acid is deconjugated bile acid. In some embodiments, the deconjugated bile acid is a bile acid that has been deconjugated by 7α-dehydroxylation or removal or a glycine or a taurine moiety. In some embodiments, the deconjugated bile acid is deoxycholic acid or lithocholic acid.

In some embodiments, the biological sample is serum, heparinized plasma, urine, tissue homogenate or cell lysate. In some embodiments, the serum, heparinized plasma or urine is obtained from a subject suspected of liver disease or liver dysfunction.

In some embodiments, the subject is a human, a dog, a cat or a horse.

According to another aspect, methods of treating a subject suffering from a condition associated with elevated levels of bile acid are provided. The methods include administering to the subject in need thereof the compositions or the pharmaceutical compositions described herein, wherein the output protein is a therapeutic protein. In some embodiments, the condition associated with elevated levels of bile acid is inflammatory bowel disease, obesity-associated hepatocellular carcinoma, a liver disease or a hepatobiliary disease. In some embodiments, the therapeutic protein is an anti-tumor protein or an anti-inflammatory protein.

According to another aspect, methods for limiting expression of a therapeutic protein or nucleic acid molecule outside of the gut are provided. The methods include operatively linking a nucleotide sequence encoding a therapeutic protein or nucleic acid molecule to the one or more operators and bacteria specific promoter in the engineered nucleic acid molecules or the expression vectors described herein.

These and other aspects and embodiments are described in further detail herein.

BRIEF DESCRIPTION OF THE DRAWINGS

The accompanying drawings are not intended to be drawn to scale. For purposes of clarity, not every component may be labeled in every drawing.

FIG. 2A shows a schematic of the bile acid sensor design. FIG. 2B shows the design with promoter/operator sequences. "BAS" ("BA Sensor") shown in FIG. 2A is a nucleotide sequence encoding the bile acid sensor BreR from *V. cholerae*, the expression of which is driven by the constitutive *B. thetaiotaomicron* promoter. BT1311 (FIG. 2B). "Nanoluc" is a nucleotide sequence encoding the luciferase NANOLUC®, driven by one of two promoters shown in FIG. 2B, PcfxA (as shown: nucleotides 44-80 of SEQ ID NO: 7, plus the 3'CGCA sequence) or PbreR (as shown: nucleotides 44-116 of SEQ ID NO: 6, plus the 3'CGCA sequence), the sequences of which are shown below the schematic construct. An operator sequence containing two copies of the BreR consensus sequence (AANGTANAC-N(6)-GTNTACNTT, SEQ ID NO: 5) in the PbreR promoter is bound by BreR, resulting in repression of transcription of the luciferase NANOLUC®. The strong PcfxA promoter lacks the operator sequence containing the BreR consensus sequences.

FIGS. 4A-4G show bile acid sensor activity. FIG. 4A shows chemical structures of various bile acid species and FIGS. 4B-4G show its respective induction of reporter measured by luminescence.

FIG. 6A is an illustration showing conversion of CA to DCA by *C. scindens*. FIG. 6B is a schematic representation of the experimental workflow. FIG. 6C shows reporter activity of the BA Sensor strain after incubated with the respective culture supernatants.

FIG. 7A is an illustration of a bile acid controlled NOT gate. FIG. 7B shows mining of *Bacteroides* RBS for tuning the repressor activity. FIG. 7C is a schematic showing synthetic *Bacteroides* promoters made for optimal operator design.

FIG. 8A shows a schematic of the bile acid sensor design. FIG. 8B shows that increasing concentrations of DCA in the media produces increased luminescence.

DETAILED DESCRIPTION OF THE DISCLOSURE

Figure 1:
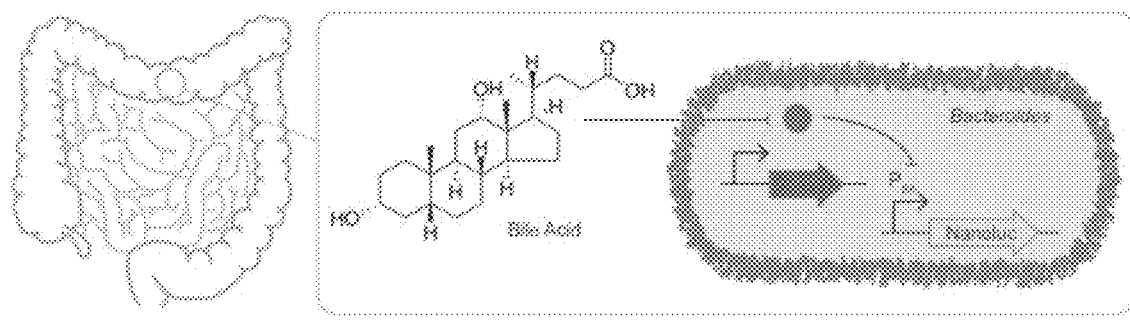
FIG. 1 shows an illustration of a transcription sensor for bile acids in the gut symbiont *Bacteroides*.

Disclosed herein is a transcriptional sensor for bile acids in the human gut symbiont *Bacteroides thetaiotaomicron* that includes a genetically engineered bile acid inducible promoter that activates the transcription of a gene (for example, a reporter gene such as NanoLuc) in the presence of deconjugated bile acids in the environment. The detailed design of engineered nucleic acid molecules containing the bile acid sensor is shown in FIG. 1. The sensor is designed based on an allosteric transcription factor in the TetR family from *Vibrio cholera*, BreR, and VFA0359 from *Vibrio fischeri*. The transcription factor BreR (and VFA0359) can bind to a specific DNA sequence (the operator) near the *Bacteroides* promoter and repress transcription of a gene by blocking RNA polymerase activity. However, in the presence of deconjugated bile acids, BreR will bind to bile acids, which leads to a conformational change, leading to the release of DNA and allowing for transcription of the gene by RNA polymerase to take place.

Bacteria have a different promoter structure than mammalian cells, and therefore bile acid sensors active in one type of organism (in particular in a different kingdom of organisms) would not be expected to function correctly. Even among bacteria, cross-species function of bile acid sensors cannot be expected per se. In particular, *Bacteroides* has a completely different promoter structure and ribosome binding site (RBS) than canonical bacterial promoters that are well-studied, and canonical promoters and RBS structures do not function in *Bacteroides*. Thus, use of bile acid sensors from one organism in another would be expected to require a complete re-design of the promoter and RBS sequence to retain function.

As demonstrated herein, BreR is a functional bile acid sensor in *Bacteroides*. This was unexpected in view of the different species, *V. cholera*, from which the BreR was obtained.

Figure 4:
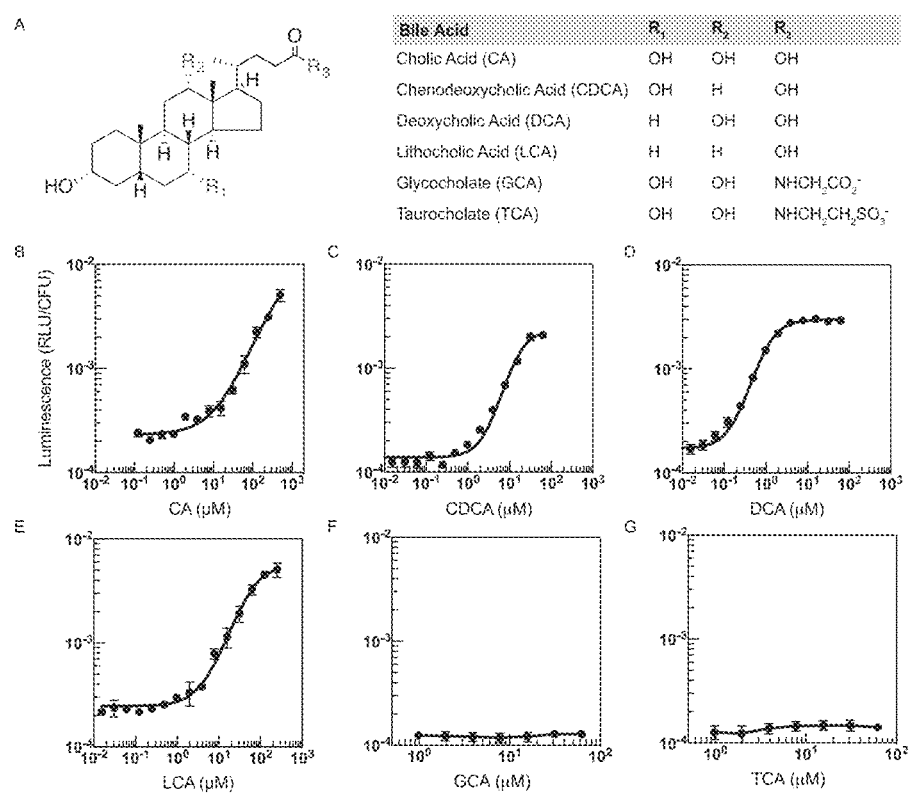
FIG. 4 shows bile acid sensor functionality in vitro. The engineered nucleic acid molecule containing the bile acid sensor was sensitive to deconjugated bile acids deoxycholic acid (DCA), lithocholic acid (LCA), chenodeoxycholic acid (CDCA), and cholic acid (CA), but not to glycocholic acid (GCA), taurocholic acid (TCA), or cholesterol. The chemical structure of each bile acid is shown above the graphs resulting from the use of that bile acid.
Figure 5:
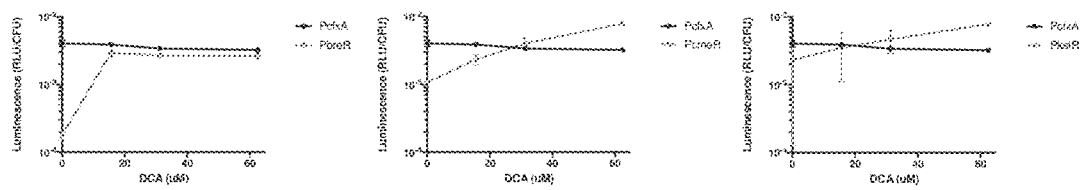
FIG. 5 shows sensitivity of the engineered nucleic acid molecule containing the bile acid sensor to DCA using BreR as the bile acid sensor protein, but not CmeR or KstR.

Another unexpected aspect of the disclosed engineered nucleic acid molecules is that other bile acid sensor proteins did not work or were not responsive to bile acids. The *V. cholerae* BreR that was used to develop the engineered nucleic acid molecules containing a bile acid sensor in *Bacteroides* is not the only bile acid sensor known in bacteria. *Campylobacter jejuni* has a bile acid sensor CmeR, *Listeria monocytogenes* has a bile acid sensor BrtA, and *Mycobacterium tuberculosis* and *Mycobacterium smegmatis* has a 3-oxo-4-cholestenoic acid sensor KstR, which is an intermediate in the cholesterol catabolism pathway, which is structurally similar to bile acids. As shown in FIG. 4, CmeR and KstR were not responsive to DCA. Unexpectedly, a homolog of BreR, VFA0359 from *Vibrio fischeri*, was found to be even more active than BreR.

It is known that mammals also have a bile acid sensor. Farnesoid X Receptor, Vitamin D receptor, and TGR5, are each known to function as a bile acid sensor, and each plays a crucial role in bile acid, cholesterol homeostasis and glucose and energy metabolism.

The disclosed method for bile acid measurement is based on use of an engineered nucleic acid molecule in which bile acid levels influence transcription of an output molecule based on the level of binding to an operator sequence operably linked to nucleotide sequence encoding the output molecule. The amount of environmental bile acids levels correlate with expression level of the output molecule, which is different that prior methods that have utilized enzymatic detection (e.g., WO 2004/076657), wherein the amount of environmental bile acids correlate with enzymatic activity. This is distinction is important because the method and compositions disclosed herein allow one to connect the genetic bile acid sensor part to other genes downstream, such as to a therapeutic output or a more complex circuitry that integrates multiple sensor inputs allowing the bacteria to compute based on the bile acid levels. This is simply not possible with the enzymatic method for measuring bile acids as described in WO 2004/076657, since the enzymatic output is not connected to transcription flux.

Engineered Microorganisms

Some aspects of the present disclosure are directed to engineered cells, such as microorganisms having engineered nucleic acid molecules that contain a bile acid sensor. An "engineered microorganism," as used herein, refers to a microorganism that does not occur in nature. Engineered microorganisms of the present disclosure, in some embodiments, contain one or more exogenous nucleic acids (i.e., nucleic acids that the microorganism would not normally contain) or nucleic acids that do not occur in nature (e.g., an engineered nucleic acid encoding a bile acid sensor, promoter/operator sensitive to the bile acid sensor, and at least one output molecule the transcription of which is controlled by the bile acid sensor sensitive promoter/operator). Accordingly, an engineered microorganism can be a microorganism that has been designed, produced, prepared, synthesized, manufactured and/or manipulated by a human.

In some embodiments, an engineered microorganism contains an engineered nucleic acid molecule. A "nucleic acid molecule" is at least two nucleotides covalently linked together, which in some instances may contain phosphodiester bonds (e.g., a phosphodiester "backbone"). An "engineered nucleic acid molecule," as used herein, is a nucleic acid molecule that does not occur in nature. It should be understood, however, that while an engineered nucleic acid molecule as a whole is not naturally-occurring, it may include nucleotide sequences that occur in nature. In some embodiments, an engineered nucleic acid molecule comprises nucleotide sequences from different organisms (e.g., from different species). Engineered nucleic acid molecules include recombinant nucleic acid molecules and synthetic nucleic acid molecules. A "recombinant nucleic acid molecule" is a molecule that is constructed by joining nucleic acids (e.g., isolated nucleic acid molecules, synthetic nucleic acid molecules or a combination thereof) and, in some embodiments, can replicate in a living cell. A "synthetic nucleic acid molecule" is a molecule that is amplified in vitro or chemically synthesized (e.g., using a nucleic acid automated synthesizer). A synthetic nucleic acid molecule can include nucleic acid molecules that are chemically modified, or otherwise modified, but can base pair with naturally-occurring nucleic acid molecules. Recombinant and synthetic nucleic acid molecules also include nucleic molecule that result from the replication of either of the foregoing.

In some embodiments, an engineered microorganism contains an exogenous independently-replicating nucleic acid molecule (e.g., an engineered nucleic acid molecule present on an episomal vector). In some embodiments, an engineered microorganism is produced by introducing a foreign or exogenous nucleic acid molecule into a cell using methods well known in the art. A nucleic acid molecule may be introduced into a cell by conventional methods, such as, for example, electroporation (see, e.g., Heiser W. C. Transcription Factor Protocols: Methods in Molecular Biology™ 2000; 130: 117-134), chemical (e.g., calcium phosphate) or lipid transfection (see, e.g., Lewis W. H., et al., Somatic Cell Genet. 1980 May; 6(3): 333-47; Chen C., et al., Mol Cell Biol. 1987 August; 7(8): 2745-2752), fusion with bacterial protoplasts containing recombinant plasmids (see. e.g., Schaffner W. Proc Natl Acad Sci USA. 1980 April; 77(4): 2163-7), transduction, conjugation, or microinjection of purified DNA directly into the nucleus of the cell (see, e.g., Capecchi M. R. Cell. 1980 November; 22(2 Pt 2): 479-88).

In some embodiments, the engineered microorganisms of the present disclosure are prokaryotes (e.g., bacterial cells). In some embodiments, the engineered microorganisms are bacterial cells. Bacterial cells of the present disclosure include bacterial subdivisions of Eubacteria and Archaebacteria. Eubacteria can be further subdivided into gram-positive and gram-negative Eubacteria, which depend upon a difference in cell wall structure. Also included herein are those classified based on gross morphology alone (e.g., cocci, bacilli). In some embodiments, the bacterial cells are Gram-negative cells, and in some embodiments, the bacterial cells are Gram-positive cells. Examples of bacterial cells of the present disclosure include, without limitation, cells from the *Cytophaga-Flavobacterium-Bacteroides* group or Bacteroidetes phylum, such as cells from *Bacteroides* spp., *Parabacteroides* spp., *Tannerella* sp., *Porphyromonas* spp. and *Prevotella* spp.

In some embodiments, the engineered microorganisms are non-pathogenic bacteria that are derived from a normal internal ecosystem such as bacterial flora. In some embodiments, the engineered microorganisms are non-pathogenic bacteria that are derived from a normal internal ecosystem of the gastrointestinal tract. Non-limiting examples of non-pathogenic bacteria that are part of the normal flora in the gastrointestinal tract include bacteria from the genera *Bacteroides, Clostridium, Fusobacterium, Eubacterium, Ruminococcus, Peptococcus, Peptostreptococcus, Bifidobacterium, Escherichia* and *Lactobacillus*.

In some embodiments, bacterial cells of the disclosure are anaerobic bacterial cells (e.g., cells that do not require oxygen for growth). Anaerobic bacterial cells include obligate anaerobic cells such as, for example, *Bacteroides* and *Clostridium* species. In humans, for example, anaerobic bacterial cells are most commonly found in the gastrointestinal tract.

In some embodiments, the engineered microorganisms, provided herein comprise an engineered nucleic acid molecule containing a bile acid sensor. A "bile acid sensor" as used herein refers to a molecule that causes a change in transcriptional activity in response to binding one or more bile acids. In some embodiments, the bile acids are deconjugated bile acids, such as deoxycholic acid (DCA), lithocholic acid (LCA), chenodeoxycholic acid (CDCA), and cholic acid (CA).

The bile acid sensors of the present disclosure, in some embodiments, are comprised of protein. The terms "protein," "peptide," and "polypeptide" are used interchangeably herein and refer to a polymer of amino acid residues linked together by peptide (amide) bonds. A protein, peptide, or polypeptide may refer to an individual protein or a collection of proteins.

The bile acid sensors of the present disclosure are transcriptional repressors that are inhibited upon binding of bile acids. For example, when the bile acid sensor is not bound to certain bile acids, it represses transcription of a nucleic acid sequence operably linked to an operator sequence in a promoter, by binding to one or more operator sequences. Conversely, when the bile acid sensor binds certain bile acids, the repressor activity is decreased, thereby permitting transcription of the nucleic acid sequence. In some embodiments, the bile acid sensors is a BreR transcriptional repressor.

For example, the bile acid sensor BreR from *V. cholerae* has been described by Cerda-Maira et al., J Bacteriol. 2013; 195:307-17): the contents of which are hereby incorporated by reference for its description of BreR. In some embodiments, the bile acid sensor comprises a BreR protein from *V. cholerae*. In some embodiments, the bile acid sensor comprises the amino acid sequence encoded by SEQ ID NO: 1. In some embodiments, the bile acid sensor consists essentially of the amino acid sequence encoded by SEQ ID NO: i. In some embodiments, the bile acid sensor consists of the amino acid sequence encoded by SEQ ID NO: 1.

In some embodiments, the bile acid sensor comprises a VFA0359 protein from *Vibrio fischeri*. In some embodiments, the bile acid sensor comprises the amino acid sequence encoded by SEQ ID NO: 2. In some embodiments, the bile acid sensor consists essentially of the amino acid sequence encoded by SEQ ID NO: 2. In some embodiments, the bile acid sensor consists of the amino acid sequence encoded by SEQ ID NO: 2.

In some embodiments, the bile acid sensor comprises a protein that is at least 70%, at least 75%, at least 80%, at least 85%, at least 90%, at least 95%, at least 98%, or at least 99% identical to a naturally-occurring BreR protein or VFA0359 protein. As used herein, such variants of BreR or VFA0359 amino acid sequence are amino acid sequences that are not identical to, but shares a degree of identity with the BreR or VFA0359 amino acid sequence described herein (e.g., encoded by SEQ ID NO: 1 or SEQ ID NO: 2). As used herein, the term the bile acid sensor protein variant has at least 70%, at least 75%, at least 80%, at least 85%, at least 90%, at least 95%, or at least 99% identity with the amino acid sequence encoded by SEQ ID NO: 1 or SEQ ID NO: 2 as determined by standard methods of comparing sequences used in the art, such as the BLAST (Basic Local Alignment Search Tool) programs of the National Center for Biotechnology Information, using default parameters.

Engineered Nucleic Acid Molecules

In some embodiments, the engineered microorganisms of the present disclosure comprise engineered nucleic acid molecules responsive to any of the bile acid sensors provided herein. An "engineered nucleic acid molecule containing a bile acid sensor" comprises nucleotide sequences that are operably linked such that the bile acid sensor protein encoded in the engineered nucleic acid molecule modulates the expression of at least one nucleic acid or gene of the engineered nucleic acid molecule. Repression of transcription of the at least one nucleic acid or gene occurs via binding of the bile acid sensor protein (e.g., BreR) to an operator sequence operably linked to the at least one nucleic acid or gene. Activation or derepression of transcription of the at least one nucleic acid or gene occurs via direct binding of bile acids to the bile acid sensor (e.g., BreR), which causes a reduction in binding of the bile acid sensor to the operator sequence operably linked to the at least one nucleic acid or gene.

In some embodiments the engineered nucleic acid molecule containing a bile acid sensor comprises a first promoter and operator that are operably linked to a nucleic acid sequence encoding an output molecule, wherein the first promoter and operator is responsive to the bile acid sensor. As one non-limiting example, in response to binding deconjugated bile acids, the binding of the transcriptional repressor BreR to the operator is inhibited, thus allowing transcription of a NANOLUC® output molecule. It should be appreciated that the engineered nucleic acid molecule containing a bile acid sensor may comprise one or more nucleic acids, which may or may not be linked.

The engineered nucleic acid molecules containing a bile acid sensor of the present disclosure may comprise one or more promoters and operators operably linked to a nucleotide sequence encoding, for example, an output molecule. A "promoter" refers to a control region of a nucleic acid sequence at which initiation and rate of transcription of the remainder of a nucleic acid sequence are controlled. A promoter may also contain sub-regions to which regulatory proteins and molecules may bind, such as RNA polymerase and other transcription factors. Promoters may be constitutive, inducible, activatable, repressible, or any combination thereof. In some embodiments, the engineered nucleic acid molecules comprises at least 1 at least 2, at least 3, at least 4, at least 5, at least 6, at least 7, at least 8, at least 9, at least 10, at least 15, at least 20, at least 30 or at least 50 promoters. In some embodiments one or more of the promoters may be a promoter containing a consensus binding sequence for the bile acid sensor, which also may be referred to herein as an operator sequence. The consensus binding sequence for the bile acid sensor as used herein is SEQ ID NO: 5, though other binding sequences that are bound by other bile acid sensors may also be used in an equivalent manner. In some embodiments, the promoter containing the consensus binding sequence for the bile acid sensor (operator) comprises or consists of a PbreR promoter (SEQ ID NO: 6).

In some embodiments the engineered nucleic acid molecules of the present disclosure comprise one or more operator sites. An "operator," "operator sequence" or the like, as used herein, refers to a segment of DNA to which a molecule (e.g., a transcriptional repressor such as BreR) binds to regulate transcription or gene expression. An operator, in some embodiments, is associated with one or more promoters to modulate transcription from the one or more promoters. In some embodiments the engineered nucleic acid molecules described herein comprise one or more operator sites. In some embodiments, the engineered nucleic acid molecules comprise at least 1, at least 2, at least 3, at least 4, at least 5, at least 6, at least 7, at least 8, at least 9, at least 10, at least 15, at least 20, at least 30 or at least 50 operator sites. In some embodiments, one or more of the operator sites comprises or consists of the nucleotide sequence of SEQ ID NO: 5, such as SEQ ID NO: 10 (in the −33 element) and SEQ ID NO: 11 (downstream of the −7 element).

A promoter drives expression or transcription of the nucleic acid sequence to which it is operatively linked. In some embodiments, the promoter is operably linked to a nucleic acid encoding an output molecule. A promoter is considered to be "operably linked" when it is in a correct functional location and orientation in relation to the nucleic acid sequence it regulates, thereby resulting in the ability of the promoter to drive transcription initiation or expression of that sequence.

A promoter may be one naturally associated with a gene or sequence, as may be obtained by isolating the 5' non-coding sequences located upstream of the coding segment of a given gene or sequence (e.g., an endogenous promoter).

In some embodiments, a coding nucleic acid sequence may be positioned under the control of a recombinant or heterologous promoter, which refers to a promoter that is not normally associated with the coding sequence in its natural environment. Such promoters may include promoters of other genes; promoters isolated from another cell type; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202 and 5,928,906).

In some embodiments, the promoters described herein are "constitutive promoters," which are promoters that are constitutively active in the cell (i.e., not regulated in response to specific stimuli). Constitutive promoters (e.g., constitutive bacterial promoters) are known in the art and include, without limitation, P32, P57, P59, Pxyl, PclpB, PrepU and PlepA.

In some embodiments, the engineered nucleic acid molecules provided herein comprise a first promoter that is operably linked to a nucleic acid sequence encoding an output molecule, wherein the first promoter is responsive to the bile acid sensor. The term "output molecule," as used herein refers to a nucleic acid or protein that is expressed in response to the state of the bile acid sensor. In some embodiments, the output molecule is expressed when the bile acid sensor is bound to a bile acid (e.g., a deconjugated bile acid). In some embodiments, the output molecule is not expressed when the bile acid sensor is not bound to a bile acid (e.g., a deconjugated bile acid), in which case the bile acid sensor is bound to an operator in the promoter region.

In some embodiments, the output molecule is a nucleic acid, a reporter polypeptide, or a therapeutic protein. In some embodiments, the output molecule is a reporter polypeptide. In some embodiments, the reporter polypeptide is a fluorescent polypeptide. Fluorescent polypeptides include, without limitation cyan fluorescent protein (e.g., AmCyan1), green fluorescent protein (e.g., EGFP, AcGFP1, and ZsGreen1), yellow fluorescent protein (e.g., ZsYellow1 and mBanana), orange fluorescent protein (e.g., mOrange and mOrange2), red fluorescent protein (e.g., DsRed, tdTomato, mStrawberry and mCherry), and far-red fluorescent protein (e.g., HcRed1, mRaspberry and mPlum). In some embodiments, the reporter polypeptide is an enzyme that converts a substrate into a detectable molecule. In some embodiments, the reporter polypeptide comprises a luciferase enzyme, such as firefly luciferase, click-beetle luciferase, *Renilla* luciferase or luciferase from *Oplophorus gracilirostris*, such as NANOLUC®. It should be appreciated that reporter polypeptides, described herein, are not meant to be limiting and that additional reporter polypeptides are within the scope of this disclosure.

In some embodiments, the output molecule is a nucleic acid. In some embodiments the output molecule is a ribonucleic acid (RNA). In some embodiments the RNA output molecule is part of a molecular reporting system, such as a reporting system described in Gredell J. A., "Protein and RNA engineering to customize microbial molecular reporting", Biotechnol J. 2012 April; 7(4):477-99; the contents of which are hereby incorporated by reference. Additional nucleic acid output molecules are within the scope of this disclosure.

In some embodiments, the output molecule is a therapeutic protein. In some embodiments, the therapeutic protein is a protein that binds tumor necrosis factor (TNF) or TNF receptors, a protein that binds integrins or integrin receptors, or fibroblast growth factor 19 (FGF19). Examples of proteins that bind TNF or TNF receptors include adalimumab (HUMIRA®), certolizumab (CIMZIA®), golimumab (SIMPONI®), and infliximab (REMICADE®) and an anti-TNF Nanobody (ozoralizumab). Examples of proteins that bind integrins include natalizumab (TYSABRI®) and vedolizumab (ENTYVIO™). Other examples of therapeutic proteins include interleukin-10 (IL-10) and the peptide linaclotide (LINZESS®).

Also provided herein are vectors comprising any of the engineered nucleic acid molecules described herein. In some embodiments, vectors comprise any of the genes, nucleic acids, and/or promoters of any of the engineered nucleic acid molecules described herein. In some embodiments, vectors comprise any of the output molecules described herein. A "vector" is a nucleic acid (e.g., DNA) used as a vehicle to artificially carry genetic material (e.g., an engineered nucleic acid molecule) into a cell where, for example, the nucleic acid can be replicated and/or expressed. In some embodiments, a vector is an episomal vector (see, e.g., Van Craenenbroeck K. et al. Eur. J. Biochem. 267, 5665, 2000, incorporated by reference herein). A non-limiting example of a vector is a plasmid. Plasmids are double-stranded generally circular DNA sequences that are capable of automatically replicating in a host cell. Plasmids typically contain an origin of replication that allows for semi-independent replication of the plasmid in the host and also the transgene insert. Plasmids may have more features, including, for example, a "multiple cloning site," which includes nucleotide overhangs for insertion of a nucleic acid insert, and multiple restriction enzyme consensus sites to either side of the insert. Another non-limiting example of a vector is a viral vector.

Applications

The engineered nucleic acid molecules and engineered microorganisms containing a bile acid sensor may be applied for use in cell-based diagnostics, such as where an engineered *Bacteroides* strain harboring the bile acid sensor can be used to monitor the levels of bile acids. When the bile acid sensor is coupled to a particular therapeutic function, such as releasing a therapeutic molecule, the sensor may be used as part of a therapeutic. Additionally, the bile acid sensor can be used as a safety switch to activate expression of a therapeutic molecule by an engineered microorganism only in the gut, by preventing the engineered microorganism from activating expression of the therapeutic molecule outside of the gastrointestinal tract.

Aspects of the disclosure relate to methods for detecting and/or treating excess or elevated bile acids in a subject comprising administering to the subject any of the engineered microorganisms provided herein. The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject is suspected of having excess or elevated bile acids relative to a normal range of bile acids known for the type of organism.

In some embodiments, the subject has or is at risk of having a disease or disorder. In some embodiments, the disease or disorder is inflammatory bowel disease, obesity-associated hepatocellular carcinoma, a liver disease or a hepatobiliary disease.

The terms "treatment," "treat" and "treating," refer to a clinical intervention aimed to reverse, alleviate, delay the onset of, or inhibit the progress of a disease or disorder or one or more symptoms thereof. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms. Treatment may also be continued after symptoms have resolved, for example, to prevent or delay their recurrence.

Accordingly, also within the scope of the disclosure are pharmaceutical compositions comprising any of the engineered microorganisms disclosed herein. The term "pharmaceutical composition," as used herein, refers to a composition that can be administrated to a subject in the context of treatment of a disease or disorder. In some embodiments, a pharmaceutical composition comprises any of the engineered microorganisms described herein, and a pharmaceutically acceptable excipient. In some embodiments the pharmaceutical compositions are in the form of a pill. The pharmaceutical composition may be in a form for oral administration that is designed to withstand passage through the stomach for delivery to the intestines, such as an enteric coating.

In some embodiments, methods for detecting excess or elevated bile acids in a subject may include administering any of the engineered microorganisms, described herein, to the subject and obtaining and/or isolating the engineered microorganisms from the subject. For example, from a biological sample (e.g., a stool sample) of the subject. The engineered microorganisms from the subject may be analyzed in vitro to determine if excess or elevated bile acids were detected in the subject. In some embodiments, the engineered microorganisms are analyzed using polymerase chain reaction (PCR), nucleic acid sequencing, measuring the level of an output molecule, or measuring fluorescence from the engineered microorganism. In some embodiments, the presence of (or an elevated level relative to background of) an output molecule, or the level of fluorescence or luminescence from the microorganism is indicative of the presence excess or elevated bile acids in the subject. In some embodiments, analysis of the engineered microorganisms is performed in vivo. Analysis of the engineered microorganisms in vivo may be performed by measuring fluorescence or luminescence from the engineered microorganisms in the gastrointestinal tract of a subject using methods known in the art, such as endoscopic methods.

EXAMPLES

Methods
Strains and Culture Conditions
*Bacteroides thetaiotaomicron* VPI-5482, *B. ovatus* ATCC 8483 and *B. fragilis* NCTC 9343 were used for this study. All *Bacteroides* strains were grown in Tryptone-Yeast Extract Glucose (TYG) broth or Brain Heart Infusion (BHI;

Difco) agar supplemented with 10% Horse Blood in the anaerobic chamber (Coy Laboratory) at 37° C. with a 5% $H_2$, 20% $CO_2$, $N_2$ (balance) gas mix. TYG broth contained 10 g/L Tryptone Peptone, 5 g/L Yeast Extract, 11 mM Glucose, 100 mM $KPO_4$ (pH7.2), 72 μM $CaCl_2$, 0.4 μg/ml $FeSO_4$ and 1 μg/mL Resazurin, 1.2 μg/ml hematin (12 mg of hematin was dissolved in 10 mL of 0.2 M histidine at pH 8 for a working stock of 1000×), 0.5 g/mL of L-cysteine, and 1 μg/ml of Vitamin K (menadione). Antibiotics were added as appropriate: erythromycin (25 μg/mL) and gentamicin (200 μg/mL). *Clostridium scindens* ATCC 35704 was routinely cultured anaerobically at 37° C. on BHIF media (Brain Heart Infusion broth supplemented with 0.02% Fructose) and BHIF agar with 10% Horse Blood. *Escherichia coli* S17-1λ pir was used to propagate *Bacteroides* shuttle vectors, and were grown at 37° C., shaking aerobically, in LB (Luria-Bertani; Difco) broth or LB agar supplemented with 100 μg/mL carbenicillin.

Construction of the Bile Acid Sensor

Briefly, the synthetic bile acid inducible promoter was constructed by placing the conserved BreR operator sequence AANGTANAC-N6-GTNTACNTT (SEQ ID NO: 5) was used in two loci, one in the −33 element (the operator sequence AATGTACACCCGTTTGTTTACTT; SEQ ID NO: 10) and one downstream of the −7 element (the operator sequence AATGTACACCCGAAAGTTTACTTT; SEQ ID NO: 11). The native cfxA RBS was replaced with rpiL*, and this synthetic promoter and rpiL* drove expression of the reporter gene Nanoluc. BreR expression was driven by a constitutive BT1311 promoter and RBS. A terminator was inserted upstream of the synthetic promoter, in between Nanoluc and the BT1311 promoter, as well as one after BreR. The *B. thetaiotaomicron* codon optimized BreR was synthesized by IDT (gBlock), and the promoter with BreR operator sequence was inserted using primers from IDT (ultramers). The above sensor fragments were assembled into a *Bacteroides* shuttle vector by Gibson Assembly and integrated into the genome of *B. thetaiotaomicron* VPI-5482 by conjugation.

The bile acid sensor using VFA 0359 from *Vibrio fischeri* was engineered by replacing BreR with VFA0359. The same operator sequences as BreR was used.

Construction of *Bacteroides* Strains Harboring the Bile Acid Sensor

*Bacteroides* shuttle vector based constructs were integrated into the *Bacteroides* genome by conjugation using *E. coli* S17-1λ pir. The *Bacteroides* shuttle vector contains a *Bacteroides* mobilizable transposon, containing an integrase gene which mediates site specific recombination at the 3' end of tRNA-Leu gene in the *B. thetaiotaomicron* genome. The *Bacteroides* shuttle vector used contains an integrase recognition site where the −2 site has been changed from a G to a C, which has been shown to increase integration frequency (Schmidt 2006). Briefly, overnight culture of *E. coli* S17-1λ pir and *Bacteroides* were subcultured 1:100 in fresh media, grown for approximately 4 hours and mixed in a 1:1 ratio in TYG and spot plated on BHI+10% horse blood agar plates. The matings were incubated aerobically at 37° C. After 24 hours, the cells were scraped, resuspended in TYG, and plated on BHI+10% horse blood agar plates supplemented with gentamicin and erythromycin. Resultant colonies that appeared after 48 hours were re-streaked on BHI+10% horse blood agar plates supplemented with gentamicin and erythromycin. Transformants were verified for site specific integration by performing PCR using primers listed in Table 1.

Luciferase Assay to Measure Bile Acid Sensor Activity

Briefly, overnight cultures of *Bacteroides* harboring the bile acid sensors were subcultured 1:100 for 7-8 hours. When cultures reached $OD_{600}$ between 0.5-0.8, 15 μL of culture was mixed with 15p L of NANOLUC® reaction buffer (with substrate added in 1:50 ratio) in a 96 well microtiter plate and its luminescence was measured using BioTek Synergy H1 Hybrid Reader. The $OD_{600}$ of 200 μL culture was also measured at the time of harvest to normalize the luminescence value to colony forming units (CFU). The final unit Relative Luminescence Unit (RLU)/CFU was calculated by dividing the raw luminescence value by CFU for 15 μL. CFU was calculated from $OD_{600}$ using a standard curve generated.

Example 1—Design of Bile Acid Sensor

Figure 2A:
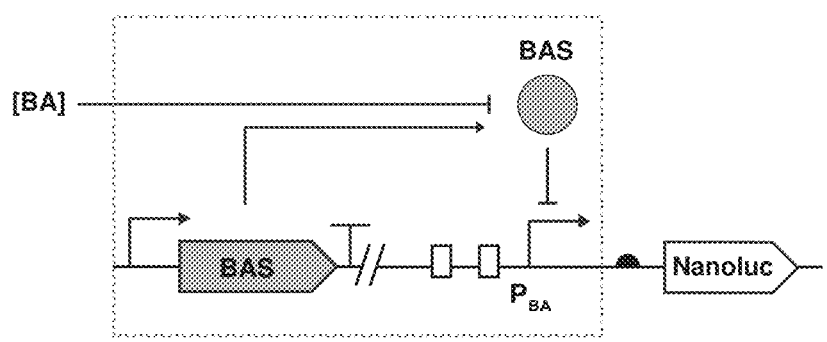
FIGS. 2A and 2B show an exemplary design of engineered nucleic acid molecules containing a bile acid sensor.
Figure 2B:
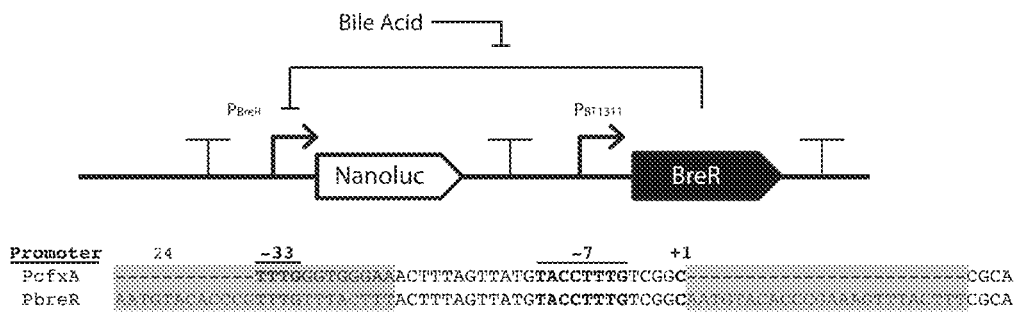

An exemplary bile acid sensor construct was constructed. The bile acid sensor construct includes a nucleic acid construct containing the bile acid sensor BreR from *V. cholerae* (Cerda-Maira et al., J Bacteriol. 2013; 195:307-17) transcribed under a constitutive *B. thetaiotaomicron* promoter, BTI311, and the target BreR operator sequence inserted around a *Bacteroides* specific promoter region driving expression of a reporter gene coding for a luciferase enzyme, NANOLUC®. NANOLUC® catalyzes the reaction of furimazine to furimamide, which releases $CO_2$ and light. FIGS. 2A and 2B show a schematic representation of the bile acid sensor nucleic acid construct.

A bile acid sensor (BAS) was first constructed in *Bacteroides thetaiotaomicron* using a known allosteric transcription factor in the tetR family which, in the absence of bile acids, binds to a specific operator DNA sequence near a promoter that represses transcription of the downstream gene. In the presence of bile acids however, the sensor binds to bile acids and changes its structural conformation, releasing DNA and allowing transcription of the downstream gene.

Expression of BreR represses transcription of the PbreR promoter, which contains the target BreR operator sequence, but not the PcfxA promoter. See FIG. 2B and FIG. 4.

Figure 3:
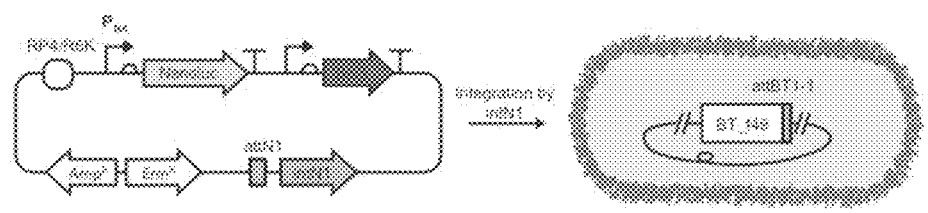
FIG. 3 shows *Bacteroides* genome integration of bile acid sensor construct.

The above sensor elements were inserted into a *Bacteroides* shuttle vector and integrated into the genome of *B. thetaiotaomicron* VPI-5482. See FIG. 3. The bile acid sensor was placed under a constitutive *Bacteroides* promoter and RBS, and the operator sequence was inserted around the promoter to create a synthetic bile acid inducible promoter driving the expression of the reporter gene NANOLUC®.

In order to assess the functionality of the engineered transcriptional bile acid sensor, the *B. thetaiotaomicron* strain harboring the engineered bile acid sensor was grown in the presence of various concentrations of bile acids available in the human gut (deoxycholic acid, DCA; lithocholic acid, LCA; cholic acid, CA; chenodeoxycholic acid. CDCA; taurocholic acid, TCA; and glycocholic acid, GCA) and the reporter gene expression was tested by measuring luminescence. As shown by the results in FIGS. 4B-4G, reporter activity is repressed in the absence of bile acids, but addition of bile acids CA, CDCA, DCA and LCA induced luminescence in a dose dependent manner. The engineered bile acid sensor does not sense conjugated bile acids TCA and GCA, at least in the concentrations that were tested, suggesting its sensitivity towards deconjugated bile acids. Among the deconjugated bile acids, the sensor was most sensitive to DCA, moderately sensitive to LCA and CDCA, and least sensitive to CA. Data is shown in Table 2 for sensitivity, basal activity, and dynamic range.

Example 2: Testing of BreR, CmeR, KstR and VFA0359

CmeR (*Campylobacter jejuni*) was expected to work as a bile acid sensor in the sensor construct, since Fussenegger and colleagues reported bile acid inducible gene expression in mammalian cells using CmeR (Rössger et al., Metab Eng. 2014 January; 21:81-90). Therefore constructs analogous to those described above in Example 1 were made using BreR, CmeR, and another bile acid sensor protein, KstR (*Mycobacterium tuberculosis*). Surprisingly, both CmeR and KstR did not show any repression of gene expression in *B. thetaiotaomicron* in the presence of deoxycholic acid (DCA), while BreR did (see FIG. 3). Therefore, BreR was the only transcriptional repressor that worked and showed induction by bile acids.

Figure 8A:
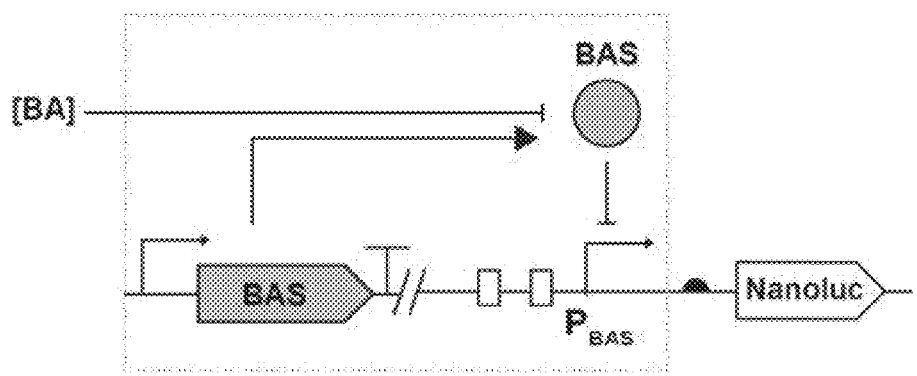
FIGS. 8A-8B show bile acid sensor design and function with VFA0359.
Figure 8B:
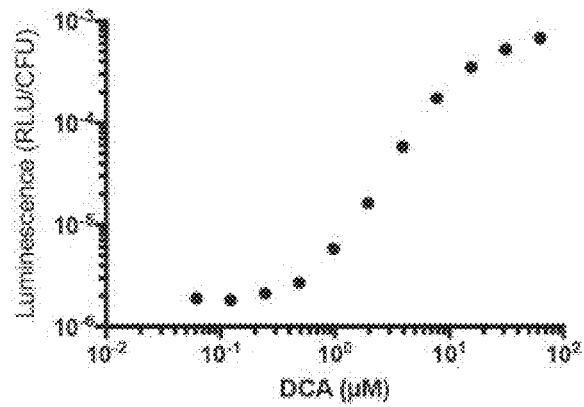

A homolog of BreR, VFA0359 from *Vibrio fischeri* was tested using the same operator sequence as used for BreR. Unexpectedly, it was found that VFA0359 also works as a bile acid sensor, and more unexpectedly induced gene expression of the reporter construct by ~600 fold. As shown in FIG. 8B, increasing concentrations of DCA in the media show increasing luminescence, suggesting that the new sensor is functional.

Example 3: BreR can Distinguish Between Conjugated and Deconjugated Bile Acids

Rössger et al. (Metab Eng. 2014 January; 21:81-90) showed that CmeR can bind to both deconjugated and conjugated bile acids, demonstrating induction by both bile acids. In contrast, BreR can distinguish between conjugated and deconjugated bile acids (see above and Cerda-Maira et al. (J Bacteriol. 2013; 195:307-17).

Figures 6A, 6B, 6C:
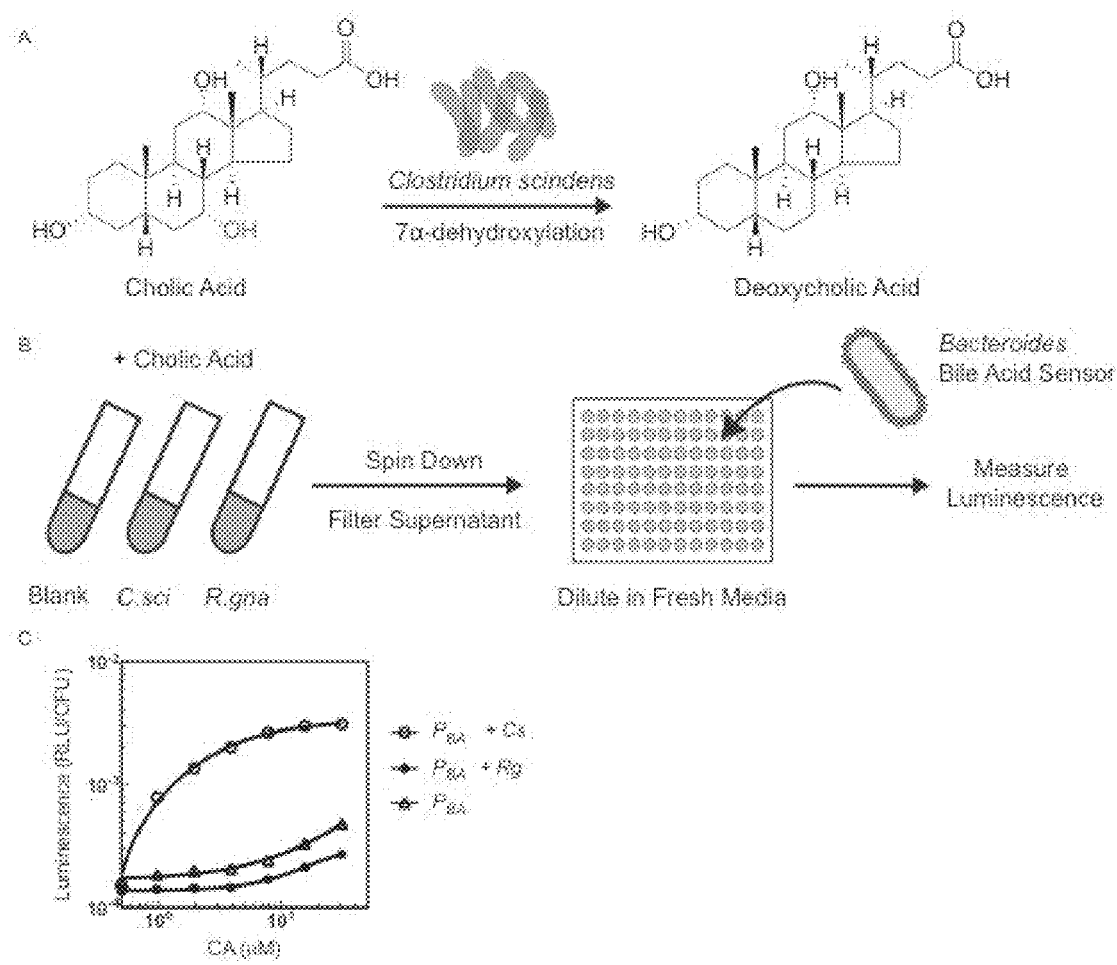
FIGS. 6A-6C show that the bile acid sensor senses the conversion of CA to DCA by *C. scindens*.
Figures 7A, 7B, 7C:
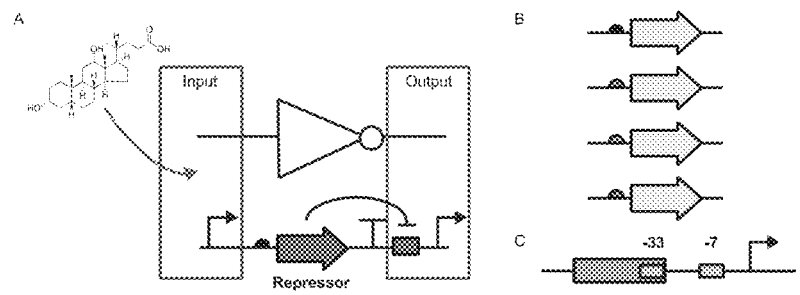
FIGS. 7A-7C show engineering of a bile acid controlled NOT gate.

When bile acids enter the colon, there they are thoroughly modified by the resident gut microbiota. The dominant actions of these resident gut bacteria include deconjugation (removal of the glycine or taurine by bile salt hydrolase) and 7α-dehydroxylation (removal of the OH group in the 7α position) of the primary bile acids CA and CDCA, yielding secondary bile acids DCA (from 7α-dehydroxylation of CA, see FIG. 6A) and LCA (from 7α-dehydroxylation of CDCA). Since the engineered bile acid sensors described herein were most sensitive to DCA and least sensitive to CA, it next was determined whether the engineered bile acid sensor can sense the conversion of CA to DCA by *Clostridium scindens*, a well-known DCA producer. As shown in FIG. 6B, *C. scindens* and *Ruminococcus gnavus* (a non 7α-dehydroxylating strain related to *C. scindens*, used as a negative control), were cultured and their supernatant was fed to the BA sensor strain and its reporter activity was measured. As shown in FIG. 6C, higher reporter activity was observed in the culture supernatant of *C. scindens*, but not in the *R. gnavus* supernatant nor the Blank media suggesting that the strain is sensing the specific conversion of CA to DCA by *C. scindens*.

The results show that BreR has higher sensitivity towards DCA than the precursor of DCA, CA. This was an unexpected (in fact, BreR being functional in *Bacteroides* itself was unexpected). Thus the BreR sensor described herein has a high sensitivity to deoxycholic acid, the bile acid linked to obesity-associated hepatocellular carcinoma.

Example 4: Engineering a Bile Acid Controlled NOT Gate

A simple NOT gate is built by using an input promoter to drive expression of a repressor, which turns off expression of an output promoter. Using the bile acid sensor described herein, a bile acid controlled NOT gate is engineered, which is a simple circuit that can take bile acids as an input signal. To build a more functional NOT gate in *Bacteroides*, RBS and promoter libraries are built to tune the repressor activity.

Figure 9:
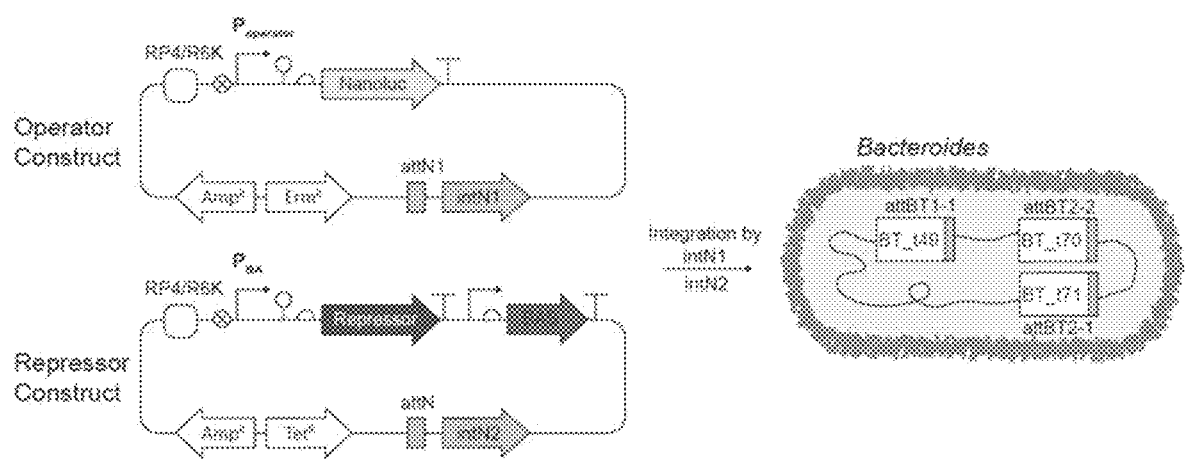
FIG. 9 shows operator and repressor constructs, and integration thereof into *Bacteroides*.
Figure 10A:
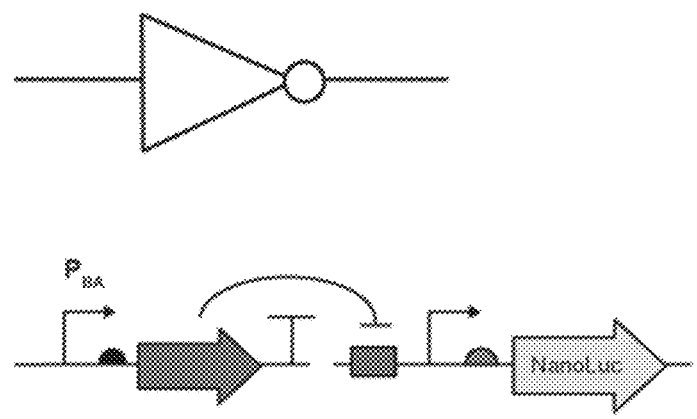
FIGS. 10A-10B show engineering of a bile acid controlled NOT gate, and results obtained.
Figure 10B:
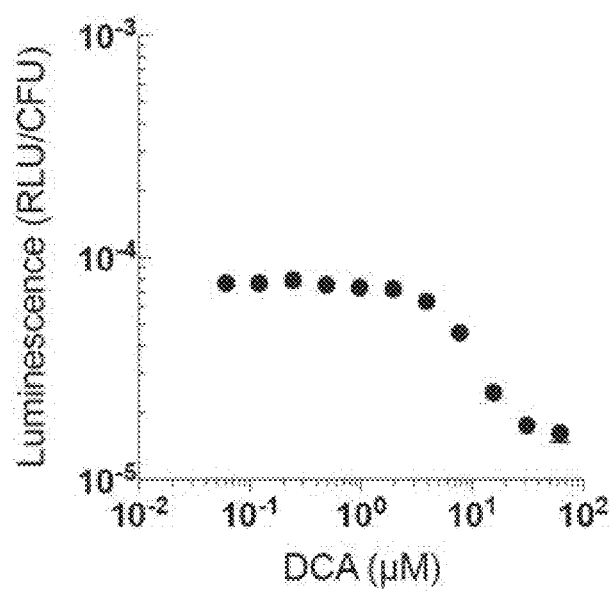

A NOT gate was engineered using the bile acid sensor to drive a BM3R1 repressor (e.g., SEQ ID NO:19; Stanton et al., Genomic mining of prokaryotic repressors for orthogonal logic gates. Nat Chem Biol. 2014 February; 10(2):99-105; Palmer et al., The repressor protein, Bm3R1, mediates an adaptive response to toxic fatty acids in *Bacillus megaterium*. J Biol Chem. 1998 Jul. 17; 273(29): 18109-16), and the cognate operator sequence was added to an output promoter driving Nanoluc transcription (see FIG. 9 and FIG. 10A). In contrast to the bile acid sensor, which showed increasing luminescence with increasing concentration of DCA, the bile acid controlled NOT gate showed that increasing concentration of DCA results in decreasing luminescence (see FIG. 10B).

TABLES

TABLE 1

Primers

| Primer | Target | Sequence | SEQ ID NO: |
|---|---|---|---|
| oMT113 | pNBU1-R | CGCTACTCTCTACGTICAACC | 12 |
| oMT114 | pNBU1-F | TGAAATACAGTGTAATTGTGGCG | 13 |
| oMT115 | BT1-1-F (also used as BV1-1-F, BO1-1-F, BF1-1-F) | TTCACTTCCATCCCGGTTCG | 14 |
| oMT116 | BT1-1-R | CACATCGCCAGGGTCCATTA | 15 |
| oMT242 | BO1-1-R | CCAACAACAAGCACACTCCA | 16 |
| oMT243 | BV1-1-A | TGCGAATGGTAGAAAAGCCC | 17 |
| oMT244 | BF1-1-R | GACCTGCAAACGACCAAAGT | 18 |

TABLE 2

Summary of Bile Acid Sensor Performance with Various Bile Acids

| Bile Acids | Sensitivity (Lum/µM*10^-5) | Basal Activity (Lum × 10^4 ± SD) | Dynamic Range (fold-change) |
|---|---|---|---|
| CA | 0.8 ± 0.2 | 2.1 ± 0.7 | 18.5 ± 3.8 |
| CDCA | 2.3 ± 1.1 | 1.9 ± 0.4 | 25.8 ± 11.1 |
| DCA | 25.8 ± 7.6 | 1.7 ± 0.8 | 71.5 ± 3.4 |
| LCA | 1.4 ± 0.8 | 2.2 ± 0.9 | 17.5 ± 4.9 |

SEQUENCES

SEQ ID NO: 1-BreR-Bt (codon optimized for use in *B. thetaiotaomicron*)
ATGAAATTGTCTGAACAGAAACGTTTGGCTTTGATCGAAGCTGCTAAAGAAGAA
TTCACTCAGTTCGGTTTCCACGCTGCTAACATGGACCGTGTATGTGAACGTGCTG
GTACTTCTAAACGTACTTTGTACCGTCACTTCACTTCTAAAGAATTGTTGTTCATC
GAAGTAATCAACTTGTTGGTAGCTCAGCCGCACAAAGTAGGTTTCGAATACCAGT
CTACTCGTTCTTTGGCTGACCAGTTGCACGACTACTTCGCTGCTAAAATCGACTTG
TTGTACCGTACTATCGGTTTGGACGTATTGCGTATGATCGTAGGTGAATTCGTAC
GTGACCCGGCTTTGACTCAGCAGTACTTGGCTTTGATGGGTACTCAGGACACTGC
TTTGACTGCTTGGTTGCAGGCTGCTATCAAAGACGGTAAATTGATCGAAAAAGAA
GTAGCTCCGATGGCTACTACTTTGATGAACTTGTTCCACGGTCAGTTCTTGTGGCC
GCAGTTGTTGGCTGCTGTAGAATTGCCGGACGCTAAACAGCAGCAGATCATGAT
GGACGAAATCATCCGTGTATTCGTATTGTCTTACGGTGTATCTTCTCCGTCTCACT
TGTCTATCGAATTGAAACCGTAA SEQ ID NO: 2-VFA0359-Bt (codon optimized for use in *B. thetaiotaomicron*)
ATGCAGAAAAAATTGACTCGTTCTCAGGAGAAACACTTGGACATCATCAACGCT
GCTAAAGAAGAATTCATCGAATTCGGTTTCTTGGCTGCTAACATGGACCGTATCA
CTTCTTCTGCTGAAGTATCTAAACGTACTTTGTACCGTCACTTCGAATCTAAAGAA
GTATTGTTCGAATCTGTATTGACTATCATCAACGACTCTGTAAACGAATCTATCTC
TTACCACTTCGACCCGAACAAATCTACTGAAGAACAGTTGACTGAAATCGCTTAC
AAAGAAATCGACGTATTGTACAAAACTTACGGTATCGCTTTGGCTCGTACTATCG
TAATGGAATTCTTGCGTCAGCCGGAAATGGCTAAAACTTTGATCCAGAACATCTA
CTCTATCCGTGCTATCACTCAGTGGTTCCGTTCTGCTATCGAAGCTAAACGTTTGA
AAGACGCTGACCCGAAATTGATGACTGACGTATACGTATCTTTGTTCCAGGGTTT
GTTCTTCTGGCCGCAGGTAATGCACTTGGACTTGGAACCGCACGGTGAAGAATTG
TCTCAGAAAATCGAAACTTTGACTACTATCTTCTTGCAGTCTTACGGTGTAGCTG
AATAA SEQ ID NO: 3-BT1311 (Constitutive promoter + RBS):
TGATCTGGAAGAAGCAATGAAAGCTGCTGTTAAGTCTCCGAATCAGGTATTGTTC
CTGACAGGTGTATTCCCATCCGGTAAACGCGGATACTTTGCAGTTGATCTGACTC
AGGAATAAATTATAAATTAAGGTAAGAAGATTGTAGGATAAGCTAATGAAATAG
AAAAAGGATGCCGTCACACAACTTGTCGGCATTCTTTTTTGTTTTATTAGTTGAAA
ATATAGTGAAAAAGTTGCCTAAATATGTATGTTAACAAATTATTTGTCGTAACTT
TGCACTCC SEQ ID NO: 4-Bacteroides consensus promoter sequence:
TTTGnnnnnn nnnnnnnnnn nnnnTAnn TTTG SEQ ID NO: 5-BreR consensus sequence:
AANGTANACNNNNNNGTNTACNTT SEQ ID NO: 6-PbreR (Bile acid inducible promoter):
TTACAAAGAAAATTCGACAAACTGTTATTTTTCTATCTATTTAAATGTACACCCGT
TTGTTTACTTTACTTTAGTTATGTACCTTTGTCGGCAATGTACACCCGAAAGTTTA
CTTT SEQ ID NO: 7-PcfxA (Constitutive promoter + RBS):
TTACAAAGAAAATTCGACAAACTGTTATTTTTCTATCTATTTATTTGGGTGGGAA
ACTTTAGTTATGTACCTTTGTCGGCAAATAAAGATATTCTCGTCAAACAAATATA
AATAATATAAAC SEQ ID NO: 8-rpiL* (RBS):
CGCATTTTAAAATAAAATAAATTATTTATTTAATTAAACGAAT SEQ ID NO: 9-NanoLuc Luciferase reporter:
ATGGTTTTTACTCTGGAAGATTTTGTTCTGCGATTGGCGTCAGACCCTCGGGTTATA
ATTTGGATCAAGTCCTGGAACAGGGTGGCGTAAGCTCTCTGTTCCAGAACCTGGG
TGTGAGCGTGACGCCGATTCAGCGCATCGTTCTGTCCGGCGAGAACGGTCTGAAA
ATTGATATTCATGTGATCATCCCGTACGAAGGCCTGAGCGCTTGACCAAATGGGTC
AAATCGAGAAATCTTTAAAGTCGTCTACCCAGTTGACGATCACCACTTCAAGGT
TATCTTGCATTACGGTACGCTGGTGATTGATGGTGTGACCCCGAATATGATTGAC
TATTTCGGCCGTCCGTATGAAGGCATTGCCGTTTTTGACGCTTAAAAAGATCACCG
TCACCGGTACCCTGTGGAATGGCAATAAGATTATTGACGAGCGTCTGATTAACCC
GGACGGCAGCCTGCTGTTCCGCGTGACCATCAACGGTGTCACGGGTTGGCGTCTG
TGCGAGCGCATCCTGGCATAA SEQ ID NO: 10-operator in the -33 element:
AATGTACACCCGTTTGTTTACTTT SEQ ID NO: 11-operator downstream of the -7 element:
AATGTACACCCGAAAGTTTACTTT SEQ ID NO: 19-BM3R1 coding sequence:
ATGGAAAGCACCCCGACCAAACAGAAAGCAATTTTTTAGCGCAAGCCTGCTGCTG
TTTGCAGAACGTGGTTTTGATGCAACCACCATGCCGATGATTGCAGAAAATGCAA
AAGTTGGTGCAGGCACCATTTATCGCTATTTCAAAAACAAAGAAAGCCTGGTGA
ACGAACTGTTTCAGCAGCATGTTAATGAATTTCTGCAGTGTATTGAAAGCGGTCT
GGCAAATGAACGTGATGGTTATCGTGATGGCTTTCATCACATTTTTTGAAGGTATG -continued

SEQUENCES

```
GTGACCTTTACCAAAAATCATCCGCGTGCACTGGGTTTTATCAAAACCCATAGCC
AGGGCACCTTTCTGACCGAAGAAAGCCGTCTGGCATATCAGAAACTGGTTGAATT
TGTGTGCACCTTTTTTCGTGAAGGTCAGAAACAGGGTGTGATTCGTAATCTGCCG
GAAAATGCACTGATTGCAATTCTGTTTGGCAGCTTTATGGAAGTGTATGAAATGA
TCGAGAACGATTATCTGAGCCTGACCGATGAACTGCTGACCGGTGTTGAAGAAA
GCCTGTGGGCAGCACTGAGCCGTCAGAGCTAA
```

REFERENCES

1. WO 2004/076657.
2. Rössger et al. (Metab Eng. 2014 January; 21:81-90.
3. Cerda-Maira. et al., Bacteriol 2013; 195:307-17.
4. Van de Wiel, et al., J. Vis. Exp. (107), e53659.

All publications, patents and sequence database entries mentioned herein, including those items listed below, are hereby incorporated by reference for the teachings referenced herein as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

Articles such as "a," "an," and "the," as used herein, may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim or another portion of the description. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. An engineered nucleic acid molecule comprising
   (a) a nucleotide sequence encoding a bile acid sensor protein that binds to a deconjugated bile acid, wherein the bile acid sensor protein is BreR or a homolog thereof, wherein the nucleotide sequence encoding the BreR or homolog thereof comprises a nucleotide sequence that is at least 95% identical to SEQ ID NO: 1 or SEQ ID NO: 2,
   (b) a *Bacteroides thetaiotaomicron* constitutive promoter that is operably linked to the nucleotide sequence encoding the bile acid sensor protein,
   (c) a nucleotide sequence encoding an output molecule, and
   (d) a *Bacteroides* specific promoter comprising SEQ ID NO: 4 that is operably linked to the nucleotide sequence encoding the output molecule, wherein the promoter further comprises one or more BreR operators to which the bile acid sensor protein can bind, and wherein the one or more BreR operators comprise the nucleotide sequence of SEQ ID NO: 5;
   wherein binding of the bile acid sensor protein to the one or more BreR operators results in inhibition of transcription of the nucleotide sequence encoding the output molecule.

2. The engineered nucleic acid molecule of claim 1, wherein the BreR is from *Vibrio cholera*.

3. The engineered nucleic acid molecule of claim 1, wherein the homolog of BreR is VFA0359 from *Vibrio fischeri*.

4. The engineered nucleic acid molecule of claim 1, wherein the deconjugated bile acid is deoxycholic acid or lithocholic acid.

5. The engineered nucleic acid molecule of claim 1, wherein the *B. thetaiotaomicron* constitutive promoter is *B. thetaiotaomicron* promoter BT1311.

6. The engineered nucleic acid molecule of claim 5, wherein the nucleotide sequence of the *B. thetaiotaomicron* promoter BT1311 is at least 95% identical to SEQ ID NO: 3.

7. The engineered nucleic acid molecule of claim 1, wherein the one or more BreR operators comprise the nucleotide sequence of SEQ ID NO:10 or SEQ ID NO: 11.

8. The engineered nucleic acid molecule of claim 1, wherein the output molecule is a protein or a nucleic acid.

9. The engineered nucleic acid molecule of claim 8, wherein the protein is a detectable protein, therapeutic protein or a transcription factor that induces the expression of a detectable molecule or therapeutic molecule.

10. An expression vector comprising the engineered nucleic acid molecule of claim 1.

11. A genetically modified *Bacteroides* bacterium comprising the engineered nucleic acid molecule of claim 1, wherein the *Bacteroides* specific promoter is active in the genetically modified *Bacteroides* bacterium in the presence of deconjugated bile acid.

12. A corn position comprising a plurality of the genetically modified *Bacteroides* bacterium of claim 11.

13. A pharmaceutical composition for oral administration comprising the composition of claim 12 and a pharmaceutically acceptable carrier.

14. A method of monitoring bile acid in the gut of a subject, the method comprising orally administering to the subject the composition of claim 12.

15. A method of determining the level of bile acid in a biological sample obtained from a subject, the method comprising incubating the composition of claim 12 with the biological sample.

16. A method of treating a subject suffering from a condition associated with elevated levels of bile acid, the method comprising orally administering to the subject in need thereof the composition of claim 12, wherein the output molecule is a therapeutic protein.

17. The genetically modified *Bacteroides* bacterium of claim 11, wherein the *Bacteroides* bacterium is *Bacteroides thetaiotaomicron*.

* * * * *

UNITED STATES PATENT AND TRADEMARK OFFICE
CERTIFICATE OF CORRECTION

PATENT NO. : 11,208,664 B2
APPLICATION NO. : 15/701498
DATED : December 28, 2021
INVENTOR(S) : Christopher A. Voigt et al.

Page 1 of 1

It is certified that error appears in the above-identified patent and that said Letters Patent is hereby corrected as shown below:

In the Claims

In Claim 12, at Column 30, Line 45:
"A corn position…"
Should read:
--A composition…--

Signed and Sealed this
Twenty-sixth Day of April, 2022

Katherine Kelly Vidal
*Director of the United States Patent and Trademark Office*